US006878523B2

(12) United States Patent
Nelson et al.

(10) Patent No.: US 6,878,523 B2
(45) Date of Patent: Apr. 12, 2005

(54) MOLECULAR INTERACTION ASSAYS ON A SOLID SURFACE

(75) Inventors: Bryce P. Nelson, Madison, WI (US); Todd C. Strother, Madison, WI (US)

(73) Assignee: Gentel Bio Surfaces, Inc., Madison, WI (US)

( * ) Notice: Subject to any disclaimer, the term of this patent is extended or adjusted under 35 U.S.C. 154(b) by 103 days.

(21) Appl. No.: 10/141,611

(22) Filed: May 8, 2002

(65) Prior Publication Data

US 2003/0211480 A1 Nov. 13, 2003

(51) Int. Cl.$^7$ .............................................. G01N 33/53
(52) U.S. Cl. ........................... 435/7.1; 435/6; 536/23.1; 530/350; 702/19; 702/20
(58) Field of Search .................. 702/19, 20; 435/6, 435/7.1; 536/23.1; 530/350

(56) References Cited

U.S. PATENT DOCUMENTS

| | | | |
|---|---|---|---|
| 5,283,173 A | 2/1994 | Fields et al. | 435/6 |
| 5,474,796 A | 12/1995 | Brennan | 427/2.13 |
| 5,618,682 A | 4/1997 | Scheirer | 435/8 |
| 5,674,713 A | 10/1997 | McElroy et al. | 435/69.7 |
| 5,858,659 A | 1/1999 | Sapolsky et al. | 435/6 |
| 5,925,525 A | 7/1999 | Fodor et al. | 435/6 |
| 5,976,796 A | 11/1999 | Szalay et al. | 435/6 |
| 5,985,551 A | 11/1999 | Brennan | 435/6 |
| 6,001,311 A | 12/1999 | Brennan | 422/131 |
| 6,017,696 A | 1/2000 | Heller | 435/6 |
| 6,045,996 A | 4/2000 | Cronin et al. | 435/6 |
| 6,051,380 A | 4/2000 | Sosnowski et al. | 435/6 |
| 6,068,818 A | 5/2000 | Ackley et al. | 422/50 |
| 6,074,859 A | 6/2000 | Hirokawa et al. | 435/189 |
| 6,110,676 A * | 8/2000 | Coull et al. | 435/6 |
| 6,127,129 A | 10/2000 | Corn et al. | 435/6 |
| 6,150,090 A * | 11/2000 | Baltimore et al. | 435/6 |
| 6,176,962 B1 | 1/2001 | Soane et al. | 156/292 |
| 6,251,676 B1 | 6/2001 | Shioda et al. | 435/455 |
| 6,361,944 B1 | 3/2002 | Mirkin et al. | 435/6 |
| 6,548,021 B1 * | 4/2003 | Church et al. | 422/68.1 |

FOREIGN PATENT DOCUMENTS

| | | |
|---|---|---|
| WO | WO 90/05305 | 5/1990 |
| WO | WO 01/61053 A2 | 8/2001 |
| WO | WO 01/87919 | 11/2001 |

OTHER PUBLICATIONS

Kako et al, Brain Res. Protocols 2: 243 (1998).*
Fields and Song, 1989, Nature, 340:245–246.
Johnston, 1987, Microbiol. Rev., 51:458–476.
Keegan et al., 1986. Science 231:699–704.
Gyuris et al., 1993, Cell, 75:791–803.
Harper et al., 1993, Cell, 75:805–816.
Vojtek et al., 1993, Cell, 74:205–214.
Anderson and Young, Quantitative Filter Hybridization, in *Nucleic Acid Hybridization* [1985].
Durfee et al., 1993, Genes Dev., 7:555–569.
deWet et al., Mol. Cell. Biol. 7:725 [1987].
Thomas et al., J. Am. Chem. Soc. 117:3830 [1995].
Frutos et al., Langmuir 16:2192 2000.
Smith et al., Langmuir 17:2502 [2001].
Chapman et al., J. Am. Chem. Soc., 122:8303 [2000].
Duffy et al., Anal. Chem., 70:4974 [1998].
Effenhauser et al., Anal. Chem., 69:3451 [1997].
Wang et al., Anal. Chem., 72:2514 [2000].
Deng et al., Anal. Chem. 72:3176 [2000].
Hu et al., Molec. Cell., 9:789 [2002].
Lee et al., Analytical Chemistry, 73:5525 [2001].

* cited by examiner

*Primary Examiner*—James Martinell
(74) *Attorney, Agent, or Firm*—Medlen & Carroll, LLP

(57) ABSTRACT

The present invention relates to novel methods for the analysis of molecular interactions. In particular, the present invention relates to compositions and methods for molecular interaction assays performed in solution and on solid surfaces. The present invention thus provides improves methods and compositions for the analysis of molecular interactions.

65 Claims, 8 Drawing Sheets

Figure 5

RNA Polymerase
Activation Domain

Small-molecule "Prey"
Here, a small molecule, such as a
potential drug, phosphate, sulfate, or
carboxylate Small-molecule "Bait"

DNA Binding Domain

5'  G  G T C C
    C G T A G C G T C A G T C G T C A G T G G A 3'
3'  C C A T C G C A G T C A G C A G T C A C C T 5'
    G C G  U A  C C G C A
    C       U A C
            C

MOLECULAR INTERACTION ASSAYS ON A SOLID SURFACE

FIELD OF THE INVENTION

The present invention relates to novel methods for the analysis of molecular interactions. In particular, the present invention relates to compositions and methods for molecular interaction assays performed in solution and on solid surfaces.

BACKGROUND OF THE INVENTION

The association and dissociation of proteins is crucial to all aspects of cell function. Examples of protein-protein interactions are evident in hormones and their respective receptors, in intracellular and extracellular signaling events mediated by proteins, in enzyme substrate interactions, in intracellular protein trafficking, in the formation of complex structures like ribosomes, viral coat proteins, and filaments, and in antigen-antibody interactions. Intracellular assays for detection of protein interactions and identification of their inhibitors have received wide attention with the completion of the human genome sequence.

One method of identifying protein-protein interactions is the yeast two-hybrid system (Fields and Song, 1989, Nature, 340:245–246). This assay utilizes the reconstitution of a transcriptional activator like GAL4 (Johnston, 1987, Microbiol. Rev., 51:458–476) through the interaction of two protein domains that have been fused to the two functional units of the transcriptional activator: the DNA-binding domain and the activation domain. This is possible due to the bipartite nature of certain transcription factors like GAL4. Being characterized-as bipartite signifies that the DNA-binding and activation functions reside in separate domains and can function in trans (Keegan et al., 1986. Science 231:699–704). The reconstitution of the transcriptional activator is monitored by the activation of a reporter gene like the lacZ gene that is under the influence of a promoter that contains a binding site for the DNA-binding domain of the transcriptional activator. This method is most commonly used either to detect an interaction between two known proteins (Fields and Song, 1989, Nature, 340:245–246) or to identify interacting proteins from a population that would bind to a known protein (Durfee et al., 1993, Genes Dev., 7:555–569; Gyuris et al., 1993, Cell, 75:791–803; Harper et al, 1993, Cell, 75:805–816; Vojtek et al., 1993, Cell, 74:205–214).

In the yeast two-hybrid system, the protein interaction must occur in yeast and must occur in the nucleus of the yeast. In addition, the yeast two hybrid assay suffers from a long lag time between assay start and detection of results, false positives and lack of control over the conditions wherein the binding partners interact. Furthermore, this system is limited to detecting protein-protein interactions. What are needed are simple, robust methods for detecting molecular interactions in a variety of situations. In particular, what is needed is an in vitro method that further amplifies the interaction signal.

SUMMARY OF THE INVENTION

The present invention relates to novel methods for the analysis of molecular interactions. In particular, the present invention relates to compositions and methods for molecular interaction assays performed in solution and on solid surfaces.

For example, in some embodiments, the present invention provides a composition comprising a solid surface, the solid surface comprising arrayed nucleic acids, at least one first protein bound to at least one of the arrayed nucleic acids, and a second protein bound to the first protein. In some embodiments, the arrayed nucleic acids comprise an array of target nucleic acid sequences. In some embodiments, the first protein is a first fusion protein, the first fusion protein comprising a DNA binding domain fused to a first binding partner, wherein the DNA binding domain is capable of binding to the target nucleic acid sequence. In some embodiments, the second protein is a second fusion protein, the second fusion protein comprising an RNA polymerase activation domain fused to a second binding partner, wherein the second binding partner is capable of interacting with the first binding partner. In some embodiments, the solid support is a metal, glass or silicon surface. In some embodiments, the metal surface is deposited on an SPR prism. In some embodiments, the array of target nucleic acid sequences comprises at least 20, preferably at least 50, even more preferably at least 100, and still more preferably at least 1000 distinct nucleic acid sequences. In some embodiments, the composition further comprises a plurality of first fusion proteins, wherein each of the plurality of fusion proteins comprises a distinct first binding partner. In some embodiments, the composition further comprises a plurality of second fusion proteins, wherein each of the plurality of fusion proteins comprises a distinct second binding partner. In some embodiments, the solid support further comprises a plurality of microfluidic channels. In some embodiments, the sold support further comprises a plurality of etched microchannels. In some embodiments, the first binding partner is selected from the group consisting of a peptide, a polypeptide, a nucleic acid, a carbohydrate, a lipid, and a small molecule. In some embodiments, the second binding partner is selected from the group consisting of a peptide, a polypeptide, a nucleic acid, a carbohydrate, a lipid, and a small molecule. In some embodiments, the composition further comprises an antibody bound to the second protein.

The present invention further provides a composition comprising a solid surface, the solid surface comprising an array of first fusion proteins, wherein each of the first fusion proteins comprises a distinct binding partner, and at least one second protein specifically bound to at least one of the first proteins. In some embodiments, the composition further comprises at least one nucleic acid target sequence bound to the first fusion protein or the second protein. In some embodiments, the first fusion protein comprises a DNA binding domain fused to the first binding partner, wherein the DNA binding domain is capable of binding to the target nucleic acid sequence. In some embodiments, first fusion protein comprises a transcription activation domain fused to the first binding partner. In some embodiments, the second protein comprises a fusion protein, the second fusion protein comprising an RNA polymerase activation domain fused to a second binding partner, wherein the second binding partner is capable of interacting with the first binding partner. In some embodiments, the second protein comprises a fusion protein, the second fusion protein comprising a DNA binding domain fused to a second binding partner, wherein the second binding partner is capable of interacting with the first binding partner. In some embodiments, the solid support is a metal surface. In some embodiments, the metal surface is deposited on an SPR prism. In some embodiments, the array of first fusion proteins comprises at least 20, preferably at least 50, even more preferably at least 100, and still more preferably at least 1000, distinct first binding partners. In some embodiments, the composition further comprises a plurality of nucleic acid target sequences, wherein each of the plurality of nucleic acid target sequences comprises a distinct nucleic acid sequence. In some embodiments, the composition further comprises a plurality of second fusion proteins, wherein each of the plurality of fusion proteins comprises a distinct second binding partner. In some embodiments, the solid support further comprises a plurality of microfluidic channels. In other embodiments, the sold support further comprises a plurality of etched microchannels. In some embodiments, the first binding partner is selected from the group consisting of a peptide, a polypeptide, a nucleic acid, a carbohydrate, a lipid and a small molecule. In some embodiments, the second binding partner is selected from the group consisting of a peptide, a polypeptide, a nucleic acid, a carbohydrate, a lipid and a small molecule. In some embodiments, the composition further comprises an antibody bound to the second protein.

The present invention further provides a composition comprising a solid surface comprising a plurality of microfluidic channels, the solid surface comprising arrayed nucleic acids, at least one first protein bound to at least one of the arrayed nucleic acids, and a second protein bound to the first protein.

The present invention also provides a composition comprising a solid surface comprising a plurality of etched microchannels, the solid surface comprising arrayed nucleic acids, at least one first protein bound to at least one of the arrayed nucleic acids, and a second protein bound to the first protein.

The present invention additionally provides a composition comprising a solid surface, the solid surface comprising arrayed nucleic acids, at least one first protein bound to at least one of the arrayed nucleic acids, a second protein bound to the first protein, and an antibody bound to the second protein.

The present invention further provides a composition comprising a solid surface comprising a plurality of microfluidic channels, the solid surface comprising an array of first fusion proteins, wherein each of the first fusion proteins comprises a distinct binding partner, and at least one second protein specifically bound to at least one of the first proteins.

The present invention also provides a composition comprising a solid surface comprising a plurality of etched microchannels, the solid surface comprising an array of first fusion proteins, wherein each of the first fusion proteins comprises a distinct binding partner, and at least one second protein specifically bound to at least one of the first proteins.

The present invention further provides a composition comprising a solid surface, the solid surface comprising an array of first fusion proteins, wherein each of the first fusion proteins comprises a distinct binding partner, at least one second protein specifically bound to at least one of the first proteins, and an antibody bound to the second protein.

The present invention also provides a composition comprising a solution of target nucleic acids, at least one first fusion bound to at least one of the nucleic acids, and a second fusion protein bound to at least one of the first proteins. In some embodiments, the composition further comprises an RNA transcribed from at least one of the target nucleic acids. In some embodiments, the first fusion protein comprises a DNA binding domain fused to a first binding partner, wherein the DNA binding domain is capable of binding to the target nucleic acid sequence. In some embodiments, the second fusion protein comprises an RNA polymerase activation domain fused to a second binding partner, wherein the second binding partner is capable of interacting with the first binding partner.

In still further embodiments, the present invention provides a system for the detection of molecular interactions, comprising a solid support comprising an array of target nucleic acid sequences; and a first fusion protein comprising a DNA binding domain fused to a first binding partner, wherein the DNA binding domain is capable of binding to the target nucleic acid sequence; and a second fusion protein comprising an RNA polymerase activation domain fused to a second binding partner, wherein the second binding partner is capable of interacting with the first binding partner. In some embodiments, the solid support is a metal surface. In some embodiments, the metal surface is deposited on an SPR prism. In some embodiments, the array of target nucleic acid sequences comprises at least 20, preferably at least 50, even more preferably at least 100, and still more preferably at least 1000 distinct nucleic acid sequences. In some embodiments, the system further comprises a plurality of first fusion proteins, wherein each of the plurality of fusion proteins comprises a distinct first binding partner. In some embodiments, the system further comprises a plurality of second fusion proteins, wherein each of the plurality of fusion proteins comprises a distinct second binding partner. In some embodiments, the system further comprises an antibody capable of specifically binding to the second fusion protein. In some embodiments, the solid support further comprises a plurality of microfluidics channels. In some embodiments, the solid support further comprises a plurality of etched microchannels. In some embodiments, the first binding partner is selected from the group consisting of a peptide, a polypeptide, a nucleic acid, a carbohydrate, a lipid and a small molecule. In some embodiments, the second binding partner is selected from the group consisting of a peptide, a polypeptide, a nucleic acid, a carbohydrate, a lipid, and a small molecule. In some embodiments, the system further comprises at least one test compound. In some embodiments, the test compound is a drug. In some embodiments, the system further comprises an apparatus capable of detecting an interaction between the first fusion protein, and the second fusion protein.

In yet other embodiments, the present invention provides system for the detection of molecular interactions, comprising a solid support comprising an array of a first fusion proteins, wherein each of the first fusion proteins comprises a DNA binding domain fused to a first binding partner; a second fusion protein comprising an RNA polymerase activation domain fused to a second binding partner, wherein the second binding partner is capable of interacting with the first binding partner; and at least one target nucleic acid sequence wherein the target sequence is capable of being bound by the DNA binding domain.

The present invention further provides a system for the detection of molecular interactions, comprising a solid support comprising an array of microfluidic channels, the sold support further comprising an array of target nucleic acid sequences; and a first fusion protein comprising a DNA binding domain fused to a first binding partner, wherein the DNA binding domain is capable of binding to the target nucleic acid sequence; and a second fusion protein comprising an RNA polymerase activation domain fused to a second binding partner, wherein the second binding partner is capable of interacting with the first binding partner.

The present invention also provides a system for the detection of molecular interactions, comprising a solid support comprising an array of etched microchannels, the solid support further comprising an array of target nucleic acid sequences; and a first fusion protein comprising a DNA binding domain fused to a first binding partner, wherein the DNA binding domain is capable of binding to the target nucleic acid sequence; and a second fusion protein comprising an RNA polymerase activation domain fused to a second binding partner, wherein the second binding partner is capable of interacting with the first binding partner.

The present invention additionally provides a system for the detection of molecular interactions, comprising a solution of at least one target nucleic acid sequence; and a first fusion protein comprising a DNA binding domain fused to a first binding partner, wherein the DNA binding domain is capable of binding to the target nucleic acid sequence; and a second fusion protein comprising an RNA polymerase activation domain fused to a second binding partner, wherein the second binding partner is capable of interacting with the first binding partner.

In still other embodiments, the present invention provides a method of detecting interactions between biological molecules, comprising providing a solid support comprising an array of target nucleic acid sequences; and a first protein capable of interacting with the target nucleic acid sequence; a second protein capable of interacting with the protein; and a system configured for the detection of RNA transcribed from the target nucleic acid sequences; and contacting the first and second fusion proteins with the solid support under conditions such that the first and second proteins are capable of interacting; detecting the presence or absence of RNA transcribed from the target nucleic acid sequence with the system, wherein the presence of the RNA is the result of an interaction between the first and second proteins. In some embodiments, the first protein comprises a first fusion protein comprising a DNA binding domain fused to a first binding partner, wherein the DNA binding domain is capable of binding to the target nucleic acid sequence. In some embodiments, first protein comprises a second fusion protein comprising an RNA polymerase activation domain fused to a second binding partner, wherein the second binding partner is capable of interacting with the first binding partner. In some embodiments, the detection system is selected from the group consisting of a fluorescence detection system, a SPR detection system, a RT-PCR detection system, an electrophoresis detection system, and a hybridization detection system. In some embodiments, the solid support is a metal surface. In some embodiments, the metal surface is deposited on an SPR prism. In some embodiments, the array of target nucleic acid sequences comprises at least 20, preferably at least 50, even more preferably at least 100, and still more preferably at least 1000 distinct nucleic acid sequences. In some embodiments, the method further comprises providing a plurality of first fusion proteins, wherein each of the plurality of fusion proteins comprises a distinct first binding partner. In some embodiments, the method further comprises providing a plurality of second fusion proteins, wherein each of the plurality of fusion proteins comprises a distinct second binding partner. In some embodiments, the solid support further comprises a plurality of microfluidics channels. In some embodiments, the first binding partner is selected from the group consisting of a peptide, a polypeptide, a nucleic acid, a carbohydrate, a lipid and a small molecule. In some embodiments, the second binding partner is selected from the group consisting of a peptide, a polypeptide, a nucleic acid, a carbohydrate, a lipid and a small molecule.

The present invention further provides a method of detecting interactions between biological molecules, comprising: providing a solid support comprising a plurality of microfluidic channels, the solid support further comprising an array of target nucleic acid sequences; and a first protein capable of interacting with the target nucleic acid sequence; a second protein capable of interacting with the protein; and a system configured for the detection of RNA transcribed from the target nucleic acid sequences; and contacting the first and second fusion proteins with the solid support under conditions such that the first and second proteins are capable of interacting; detecting the presence or absence of RNA transcribed from the target nucleic acid sequence with the system, wherein the presence of the RNA is the result of an interaction between the first and second proteins.

The present invention also provides a method of detecting interactions between biological molecules, comprising: providing a solid support comprising a plurality of etched microchannels, the solid support further comprising an array of target nucleic acid sequences; and a first protein capable of interacting with the target nucleic acid sequence; a second protein capable of interacting with the protein; and a system configured for the detection of RNA transcribed from the target nucleic acid sequences; and contacting the first and second fusion proteins with the solid support under conditions such that the first and second proteins are capable of interacting; detecting the presence or absence of RNA transcribed from the target nucleic acid sequence with the system, wherein the presence of the RNA is the result of an interaction between the first and second proteins.

The present invention additionally provides a method of detecting interactions between biological molecules, comprising: providing a solid support comprising an array of target nucleic acid sequences; and a first protein capable of interacting with the target nucleic acid sequence; a second protein capable of interacting with the protein; and a system configured for the label-free detection of RNA transcribed from the target nucleic acid sequences; and contacting the first and second fusion proteins with the solid support under conditions such that the first and second proteins are capable of interacting; detecting the presence or absence of RNA transcribed from the target nucleic acid sequence with the system, wherein the presence of the RNA is the result of an interaction between the first and second proteins.

In some embodiments, the present invention provides a method of detecting molecular interactions, comprising: providing a solid surface comprising an array of first proteins; at least one second protein; a system configured for detecting an interaction of the first protein and the second protein; and contacting the second proteins with the first protein array under conditions such that the first and second proteins are capable of interacting; detecting the interaction of the first protein and the second protein using the system.

The present invention also provides a method of detecting molecular interactions, comprising: providing a surface comprising an array of first proteins; at least one second protein, the second protein comprising an epitope for an antibody; an antibody; a system configured for detecting an interaction of the second protein and the antibody; and contacting the second protein with the first protein array under conditions such that the first and second proteins are capable of interacting; contacting the antibody with the second protein; and detecting the interaction of the second protein and the antibody using the system.

The present invention further provides a method of detecting molecular interactions, comprising providing a solid surface comprising an array of target nucleic acids; at least one first protein; at least one second protein, the second protein further comprising an epitope for an antibody; at least one antibody; and a system configured for detecting an interaction of the second protein and the antibody; and contacting the first protein and the second protein under conditions such that the first and second proteins are capable of interacting; contacting the interacting first and second proteins with the arrayed nucleic acids; contacting the at least one antibody with the second protein; and detecting the interaction of the first protein and the second protein using the apparatus.

The present invention also provides a method of detecting interactions between biological molecules, comprising: providing at least one target nucleic acid sequence in solution; and a first protein capable of interacting with the target nucleic acid sequence; a second protein capable of interacting with the protein; and a system configured for the detection of RNA transcribed from the target nucleic acid sequences, wherein the system comprises a solid support configured for the detection of the RNA transcribed from the target nucleic acid sequence; and contacting the first and second fusion proteins with the target nucleic acid solution under conditions such that the first and second proteins are capable of interacting; detecting the presence or absence of RNA transcribed from the target nucleic acid sequence with the system, wherein the presence of the RNA is the result of an interaction between the first and second proteins.

The present invention further provides a method of screening compounds, comprising providing a solid support comprising an array of target nucleic acid sequences; and a first fusion protein comprising a first binding partner fused to a DNA binding domain, wherein the DNA binding domain is capable of binding to the target nucleic acid sequence; a second fusion protein comprising an RNA polymerase activation domain fused to a second binding partner, wherein the second binding partner is capable of interacting with the first binding partner; a system configured for the detection of RNA transcribed from the target nucleic acid sequences; and at least one test compound; and contacting the test compound, and the first and second fusion proteins with the solid support under conditions such that the first and second binding partners are capable of interacting; detecting the presence or absence of RNA transcribed from the target nucleic acid sequence using the system, wherein the presence of the RNA is the result of an interaction between the first and second binding partners. In some embodiments, the method further comprises the step of comparing the level of RNA transcribed from the target nucleic acid sequence in the presence of the test compound to the level of transcription in the absence of the test compound. In some embodiments, the test compound is a drug. In some embodiments, the detection system is selected from the group consisting of a fluorescence detection system, a SPR detection system, a RT-PCR detection system, an electrophoresis detection system, and a hybridization detection system. In some embodiments, the solid support is a metal surface.

The present invention further provides a method of screening compounds, comprising: providing a solid support comprising a array of first proteins; at least one second protein, wherein the second protein is capable of interacting with the first protein; at least one target nucleic acid sequence, wherein the target nucleic acid sequence is capable of interacting with the array of first proteins; and a system configured for the detection of RNA transcribed from the target nucleic acid sequences; and at least one test compound; and contacting the test compound, and the first and second fusion proteins with the solid support under conditions such that the first and second binding partners are capable of interacting; detecting the presence or absence of RNA transcribed from the target nucleic acid sequence using the system, wherein the presence of the RNA is the result of an interaction between the first and second binding partners.

DESCRIPTION OF THE FIGURES

FIG. 5 shows a schematic of the interaction of first and second fusion proteins comprising small molecule binding partners and includes the GAL-4 promoter sequence (SEQ ID NO: 1).

DEFINITIONS

As used herein, the term "solid surface" refers to any solid surface suitable for the attachment of biological molecules and the performance of molecular interaction assays. Surfaces may be made of any suitable material (e.g., including, but not limited to, metal, glass, and plastic) and may be modified with coatings (e.g., metals or polymers).

As used herein, the term "substrate" refers to any material with a surface that may be coated with a film.

As used herein, the phrase "coated with a film" in regard to a substrate refers to a situation where at least a portion of a substrate surface has a film arrayed on it (e.g. through covalent or non-covalent attachment).

As used herein, the term "microarray" refers to a solid surface comprising a plurality of addressed biological macromolecules (e.g., nucleic acids or antibodies). The location of each of the macromolecules in the microarray is known, so as to allow for identification of the samples following analysis.

As used herein, the term "array of first fusion proteins" refers to a microarray of polypeptides on a solid support.

As used herein, the term "SPR surface" refers to a solid surface that is suitable for use in SPR detection. In some embodiments, "SPR surfaces" are "SPR prisms."

As used herein, the term "disposable arrayed SPR prism" refers to a prism that is suitable for use in SPR detection, comprises an arrayed surface (e.g., a microarray), and is not intended to be reused for multiple detection assays. In some embodiments, the disposable arrayed prisms are those disclosed herein.

Figure 1:
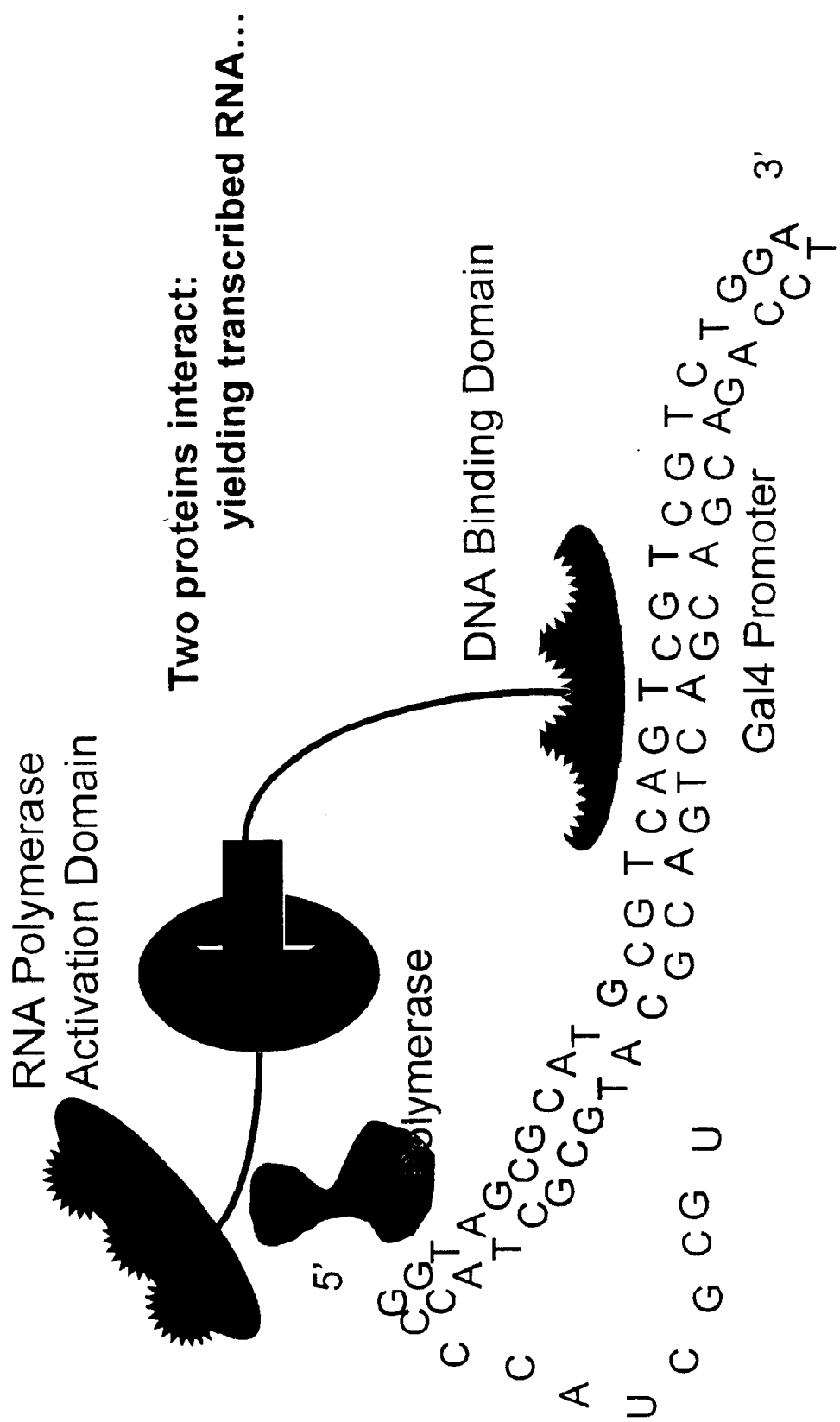
FIG. 1 shows an overview of a two-hybrid assay utilized in some embodiments of the present invention and includes the GAL-4 promoter sequence (SEQ ID NO:1).
Figure 2:
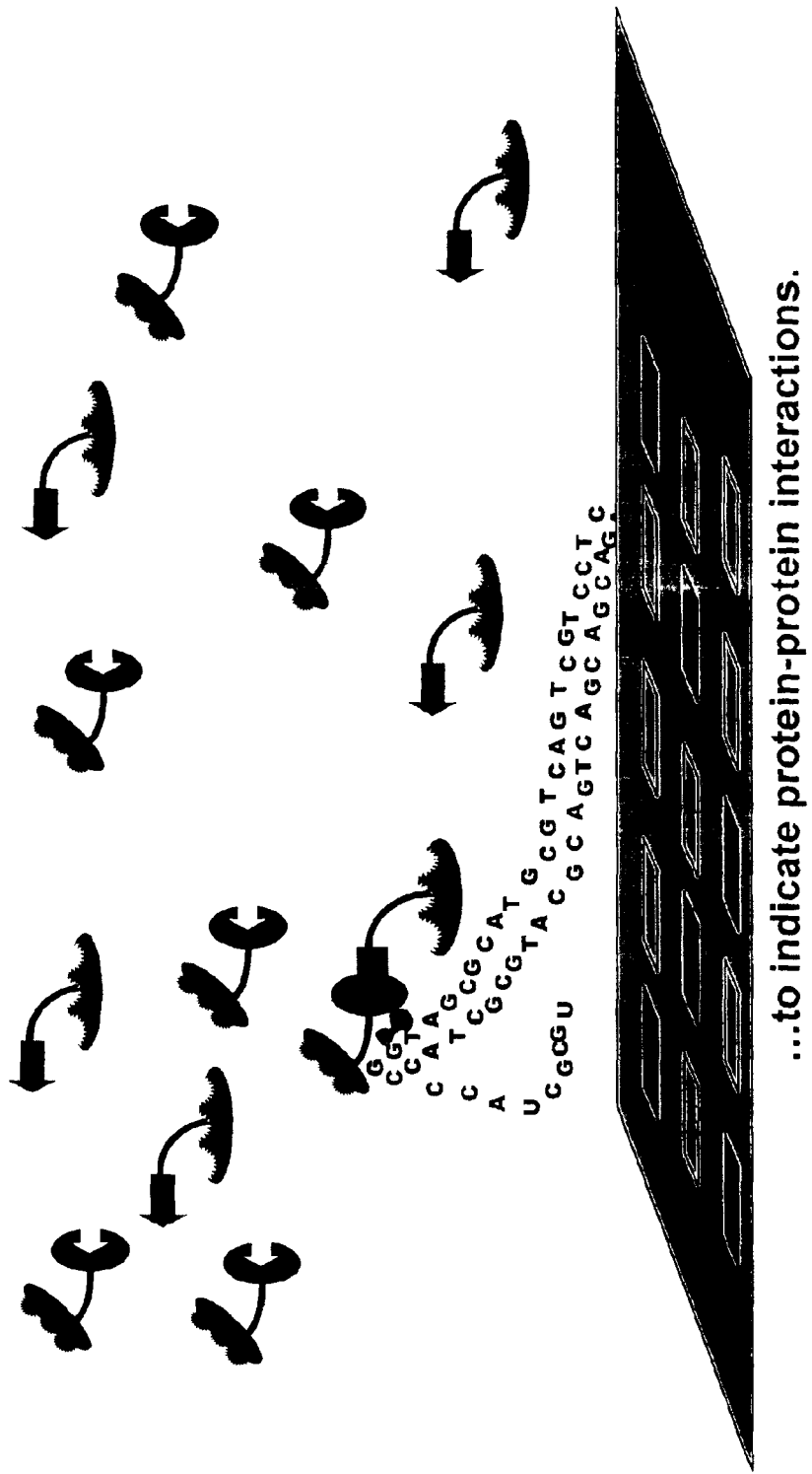
FIG. 2 shows a schematic of the detection of RNA transcripts on a solid support utilized in some embodiments of the present invention and includes the GAL-4 promoter sequence (SEQ ID NO:1).
Figure 3:
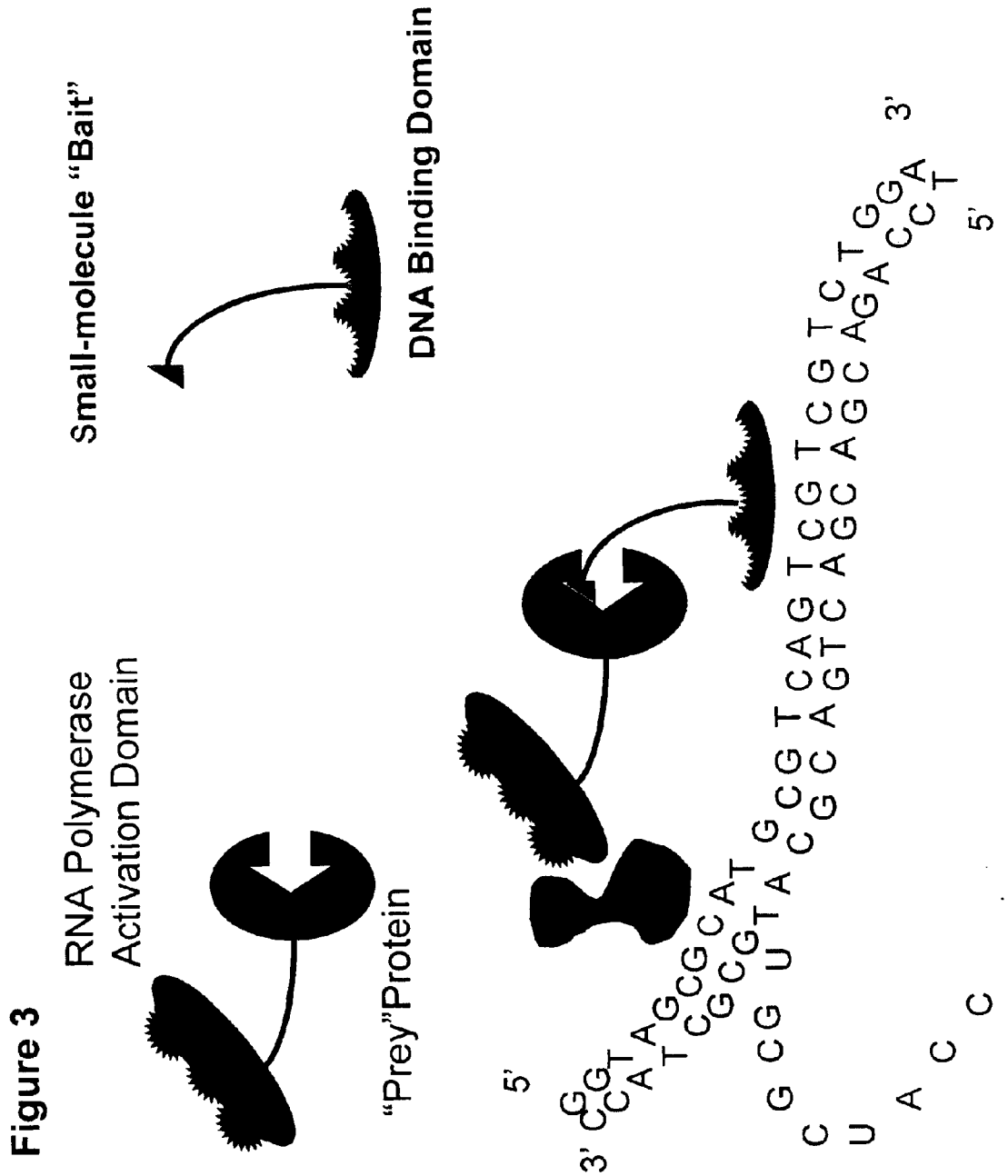
FIG. 3 shows a schematic of the interaction of a fusion protein comprising a protein binding partner with a second fusion protein comprising a small molecule binding partner and includes the GAL-4 promoter sequence (SEQ ID NO:1).
Figure 4:
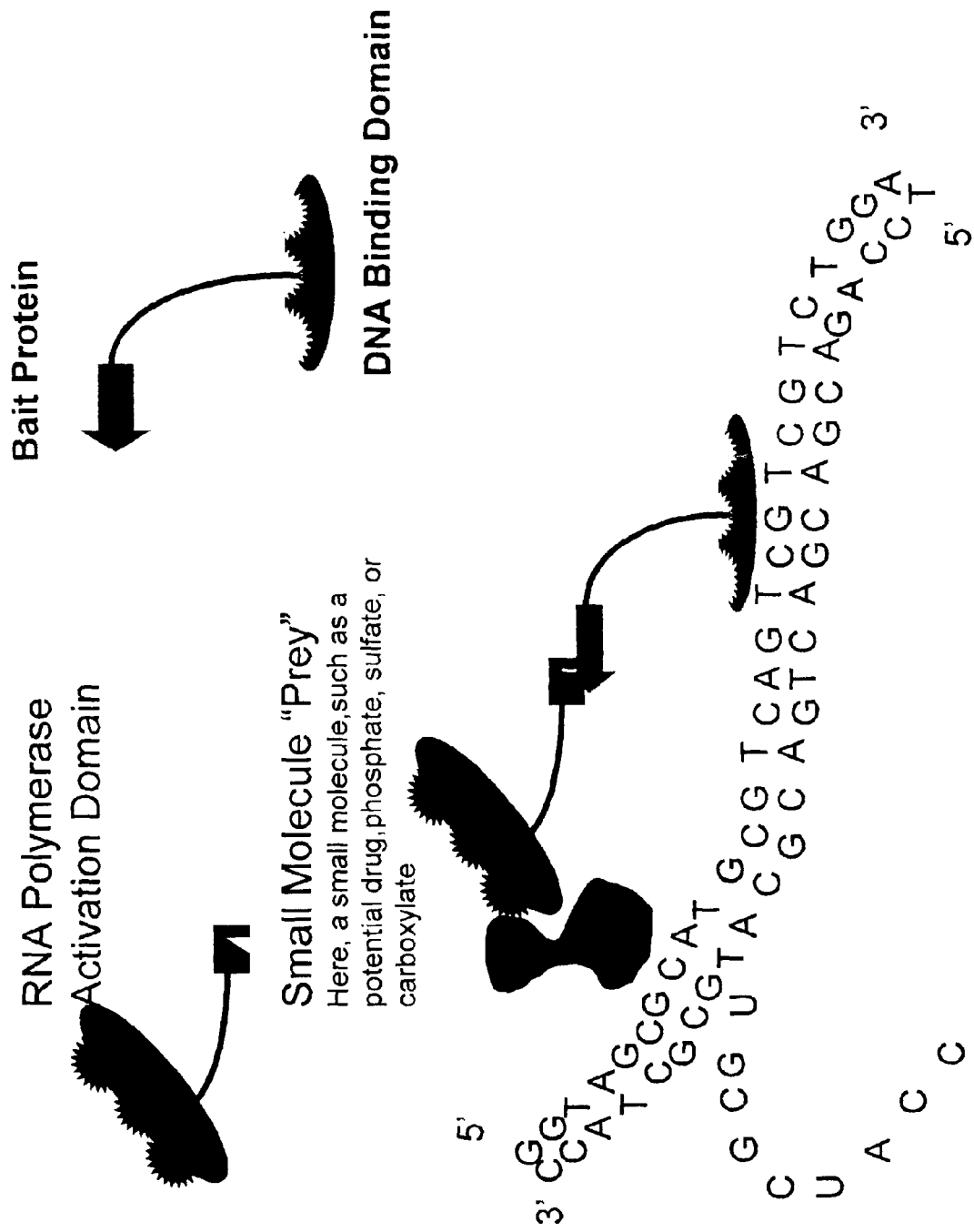
FIG. 4 shows a schematic of the interaction of a fusion protein comprising a small molecule binding partner with a second fusion protein comprising a protein binding partner and includes the GAL-4 promoter sequence (SEQ ID NO:1).
Figure 6:
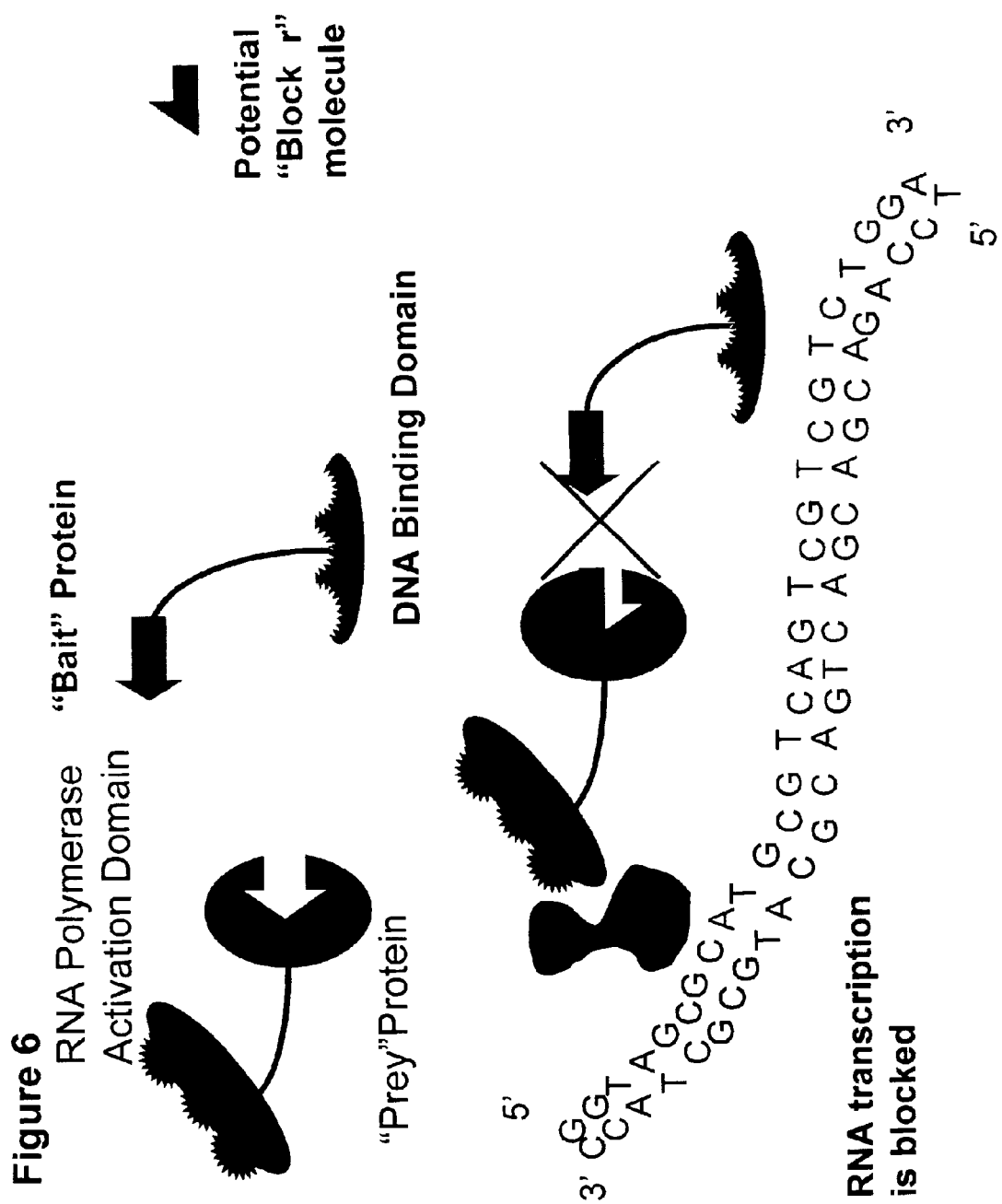
FIG. 6 shows a schematic of a screening assay used in some embodiments of the present invention and includes the GALA promoter sequence (SEQ ID NO:1).
Figure 7:
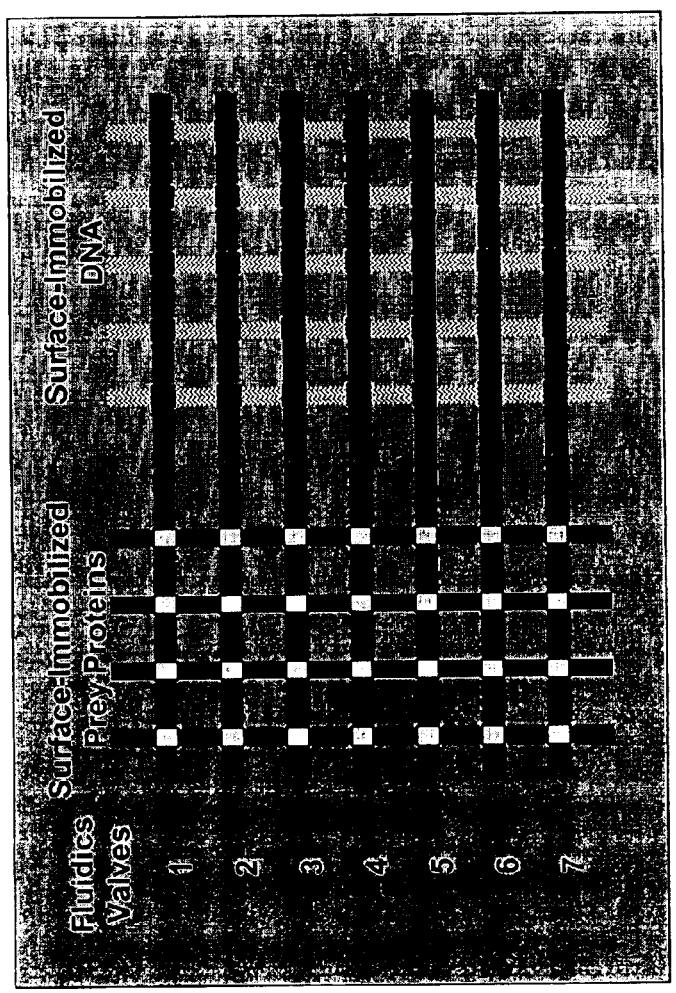
FIG. 7 shows a schematic of a high throughput assay used in some embodiments of the present invention.
Figure 8:
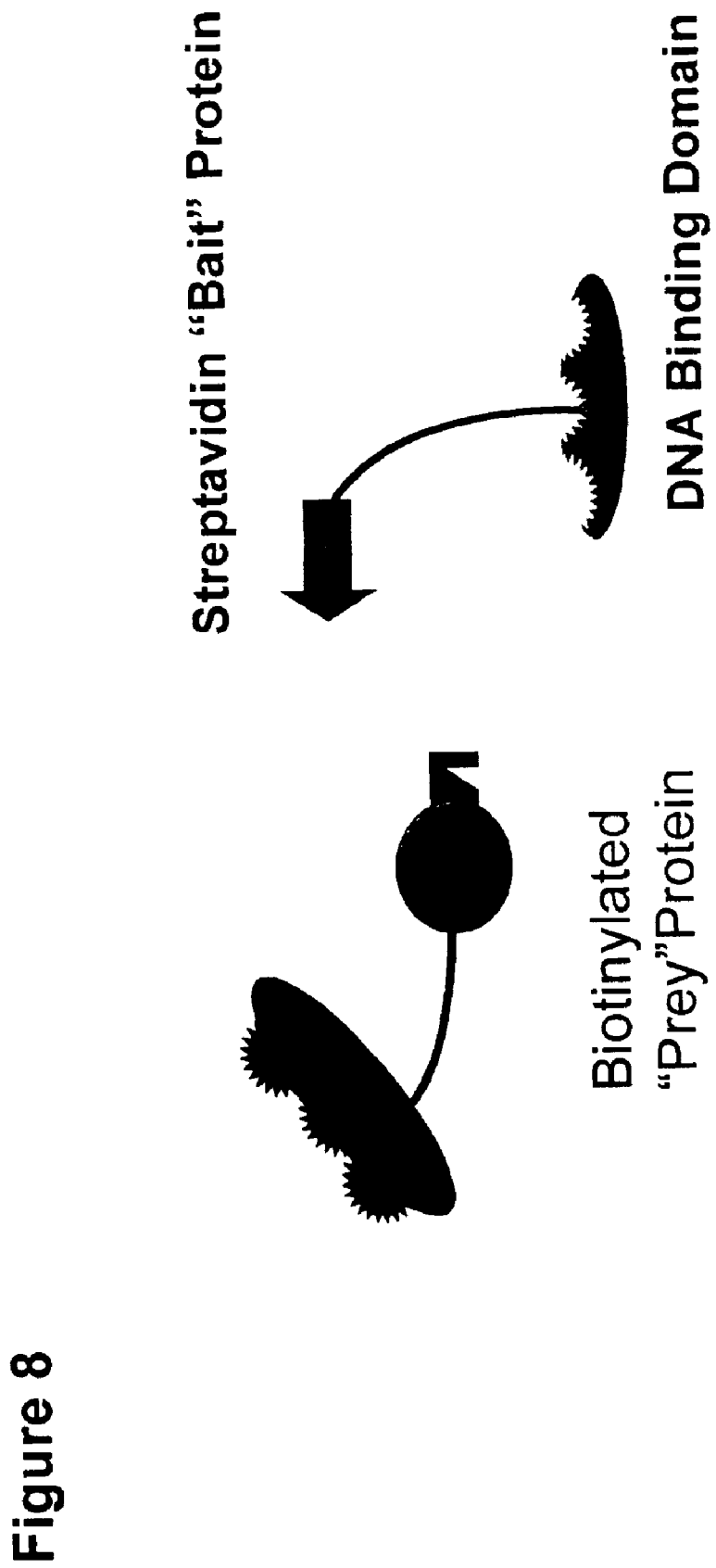
FIG. 8 shows an exemplary interaction of two fusion proteins.

As used herein, the term "coated on one face" when used in reference to an SPR prism, refers to a prism with a coating on one of the main faces of the prism. For example, the triangular prism shown in FIG. 1 is coated on the upward facing surface.

As used herein, the term "SPR capable metal film" refers to any metallic film that is suitable for use in SPR detection. Examples include, but are not limited to, gold and silver.

As used herein, the term "microfluidics channels" refers to three-dimensional channels created in material deposited on a solid surface. In some embodiments, microchannels are composed of a polymer (e.g., polydimethylsiloxane). Exemplary methods for constructing microchannels include, but are not limited to, those disclosed herein.

As used herein, the term "one-dimensional line array" refers to parallel microfluidic channels on top of a surface that are oriented in only one dimension.

As used herein, the term "two dimensional arrays" refers to microfluidics channels on top of a surface that are oriented in two dimensions. In some embodiments, channels are oriented in two dimensions that are perpendicular to each other.

As used herein, the term "microchannels" refers to channels etched into a surface. Microchannels may be one-dimensional or two-dimensional.

As used herein, the term "biological macromolecule" refers to large molecules (e.g., polymers) typically found in living organisms. Examples include, but are not limited to, proteins, nucleic acids, lipids, and carbohydrates.

As used herein, the term "target molecule" refers to a molecule in a sample to be detected. Examples of target molecules include, but are not limited to, oligonucleotides (e.g. containing a particular DNA binding domain recognition sequence), viruses, polypeptides, antibodies, naturally occurring drugs, synthetic drugs, pollutants, allergens, affector molecules, growth factors, chemokines, cytokines, and lymphokines.

As used herein, the term "binding partners" refers to two molecules (e.g., proteins) that are capable of, or suspected of being capable of, physically interacting with each other. As used herein, the terms "first binding partner" and "second binding partner" refer to two binding partners that are capable of, or suspected of being capable of, physically interacting with each other.

As used herein, the term "wherein said DNA binding domain is capable of binding to said target nucleic acid sequence" refers to a DNA binding domain that is known to, or is suspected of, binding to a particular target nucleic acid sequence.

As used herein, the term "wherein said second binding partner is capable of interacting with said first binding partner" refers to first and second binding partners that are known, or are suspected of being able to interact. The interaction may be any covalent or non-covalent (e.g., hydrophobic or hydrogen bond) interaction.

As used herein, the term "DNA binding domain" refers to the portion of a multimeric transcription factor (e.g., GAL-4 transcription factor) that binds to a specific region of a promoter DNA sequence (e.g., GAL-4 promoter).

As used herein, the term "transcription activation domain" refers to the portion of a multimeric transcription factor that, when bound to the DNA binding domain, activates transcription from a promoter DNA sequence.

The term "sample" as used herein is used in its broadest sense and includes, but is not limited to, environmental, industrial, and biological samples. Environmental samples include material from the environment such as soil and water. Industrial samples include products or waste generated during a manufacturing process. Biological samples may be animal, including, human, fluid (e.g., blood, plasma and serum), solid (e.g., stool), tissue, liquid foods (e.g., milk), and solid foods (e.g., vegetables).

The term "signal" as used herein refers to any detectable effect, such as would be caused or provided by an assay reaction. For example, in some embodiments of the present invention, signals are SPR or fluorescent signals. In other embodiments, the presence of an RNA synthesized from a gene of interest is the signal.

DNA molecules are said to have "5' ends" and "3' ends" because mononucleotides are reacted to make oligonucleotides or polynucleotides in a manner such that the 5' phosphate of one mononucleotide pentose ring is arrayed on the 3' oxygen of its neighbor in one direction via a phosphodiester linkage. Therefore, an end of an oligonucleotides or polynucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream", or 5', of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, urea, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85-100% identity, preferably about 70-100% identity). With medium stringency conditions, nucleic acid base pairing will occur between nucleic acids with an intermediate frequency of complementary base sequences (e.g., hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5× Denhardt's reagent and 100 μg/ml denatured salmon sperm DNA followed by washing in a solution comprising 0.1× SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5× Denhardt's reagent and 100 μg/ml denatured salmon sperm DNA followed by washing in a solution comprising 1.0× SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 μg/ml denatured salmon sperm DNA followed by washing in a solution comprising 5×SSPE, 0.1% SDS at 42° C. when a probe of about 500 nucleotides in length is employed.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular nucleic acid sequences.

The term "gene" refers to a nucleic acid (e.g., DNA) sequence that comprises coding sequences necessary for the production of a polypeptide, RNA (e.g., including but not limited to, mRNA, tRNA and rRNA) or precursor (e.g., precursors). The polypeptide, RNA, or precursor can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In particular, the term "gene" refers to the full-length nucleotide sequence. However, it is also intended that the term encompass fragments of the sequence, as well as other domains within the full-length nucleotide sequence. Furthermore, the terms "nucleotide sequence" or "polynucleotide sequence" encompasses DNA, cDNA, and RNA (e.g., mRNA) sequences.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the term "reporter gene" refers to a gene encoding a protein or nucleic acid that may be assayed. Examples of reporter genes include, but are not limited to, luciferase (See, e.g., deWet et al., Mol. Cell. Biol. 7:725 [1987] and U.S. Pat. Nos., 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase. Nucleic acid reporter genes comprise any sequence of sufficiently unique bases so as to be discriminated from other reporter genes by their hybridization parameters.

DETAILED DESCRIPTION

This present invention overcomes many of the drawbacks of conventional in vivo two-hybrid assay systems by replacing the nucleus or cytoplasm of a living cell as the interaction and detection matrix with a highly controllable in vitro interaction and detection system. In some embodiments, the methods of the present invention replace the mechanism for the detection of an interaction from a color change or colony growth, to the detection of expressed RNA. In addition, because interactions occur in vitro, interactions other than protein-protein interactions can be assayed.

The methods of the present invention combine an in vitro approach to detection of interactions between molecules with DNA chip-based methodology. The replacement method utilizes DNA chip technology to perform parallel experiments for detection of biomolecular interactions.

The description below provides non-limiting examples of methods and compositions for performing the assays of the present invention. The present invention is not limited to the particular methods or examples disclosed herein.

I. Solid Supports

In some preferred embodiments, the present invention utilizes solid supports for performing molecular interaction assays. The present invention is not limited to a particular solid support. Any number of solid supports may be utilized, including, but not limited to, protein or DNA "chips" composed of any number of suitable materials, and SPR (e.g., metal) surfaces. In some preferred embodiments, solid supports contain arrays of biological macromolecules (e.g., nucleic acids).

A. Chips

In some embodiments, the solid support is a "chip." Chips may be made of any suitable material including, but not limited to, metal, plastic, polymer, and glass. Several commercial sources for chips, with and without already arrayed biological molecules, exist (See e.g., the following discussion of arrays). Commercial sources include, but are not limited to, Motorola, Schaumburg, Ill.; ACLARA BioSciences, Inc., Hayward, Calif.; Agilent Technologies Inc., Palo Alto, Calif.; Aviva Biosciences Corp., Dan Diego, Calif.; Caliper Technologies Corp., Palo Alto, Calif.; Clontech, Palo Alto, Calif.; Corning, Acton, Mass.; Gene Logic Inc., Columbia, Md.; Hyseq Inc., Sunnyvale, Calif.; Incyte Genomics, Palo Alto, Calif.; Micronics Inc., Redmond, Wash.; Mosaic Technologies, Waltham, Mass.; OriGene Technologies, Rockville, Md.; Packard Instrument Corp., Meriden, Conn.; Rosetta Inpharmatics, Kirkland, Wash.; and Sequenom, San Diego, Calif.

B. SPR Surfaces

Surface Plasmon Resonance techniques involve a surface coated with a thin film of a conductive metal, such as gold, silver, chrome or aluminum, in which electromagnetic waves, called Surface Plasmons, can be induced by a beam of light incident on the metal glass interface at a specific angle called the Surface Plasmon Resonance angle. Modulation of the refractive index of the interfacial region between the solution and the metal surface following binding of the captured macromolecules causes a change in the SPR angle which can either be measured directly or which causes the amount of light reflected from the underside of the metal surface to change. Such changes can be directly related to the mass and other optical properties of the molecules binding to the SPR device surface. Several biosensor systems based on such principles have been disclosed (See e.g., WO 90/05305, herein incorporated by reference).

Generally, in a Kretschman-configuration SPR device, a glass cover slip or slide of appropriate refractive index is coated with a thin (on the order of 50 nm) SPR-capable metal layer. This metal surface is then chemically or physically patterned, and probe molecules are arrayed on the pattern features. The patterning can be either a basic grid-like array, or microfluidic channels can be overlaid onto the surface for probe deposition and sample application. This gold coated, patterned slide is then optically linked to a prism. This linkage is accomplished by placing a thin film of index-matching fluid between the prism and the slide. A sample solution is then passed over the probes arrayed on the surface. Interaction of an analyte in the solution with a probe molecule on the surface is detected as a change in refractive index. Importantly, SPR detection is label-free.

In some embodiments, a disposable SPR prism is utilized. The prism may be made of any suitable material including, but not limited to, glass and silica. In preferred embodiments, prisms are made of a high refractive index material. Preferred materials are those whose SPR minimum falls within an angle range. The range can be determined by applying known formulas (See e.g., Hansen, W. N. Journal of the Optical Society of America 53(3):380–390). For example, in some embodiments, prisms are made from a material including, but not limited to, silicon, BK-7 glass, SFL-6 glass, and preferably SF-10 glass.

In some embodiments, the prisms are coated on one face with an SPR-capable metal layer. The present invention is not limited to a particular type of metal. Any metal that is suitable for use in SPR may be utilized including, but not limited to, gold, silver, chrome or aluminum. The thickness of the metal film is not overly critical insofar as the film is uniformly applied and will function in SPR imaging analysis. In preferred embodiments, a gold film of about 450 Å thick is used. In preferred embodiments, gold is utilized as the SPR capable film to coat the prisms.

In some embodiments, the metal (e.g., gold) layer is chemically patterned for attachment of molecular probes (e.g., biomolecules). The present invention is not limited to a particular biological macromolecule. A variety of biological macromolecules are contemplated including, but not limited to, DNA, proteins, carbohydrates, lipids and amino acids.

C. Arrays

In some embodiments, solid surfaces are chemically or physically patterned for attachment of biological macromolecules (e.g., nucleic acids or proteins). In some embodiments, the present invention further provides solid supports comprising arrays of biological macromolecules. In preferred embodiments, arrays comprise at least 50, preferably at least 100, even more preferably at least 1000, still more preferably, at least 10,000, and yet more preferably, at least 100,000 distinct biological macromolecules. In preferred embodiments, each distinct biological macromolecule is addressed to a specific location on the array. In preferred embodiments, each addressable location is larger than 25, and preferably, larger than 50 microns.

The present invention is not limited to a particular method of fabricating or type of array. Any number of suitable chemistries known to one skilled in the art may be utilized.

1. Amine Modified Surface Arrays

In some preferred embodiments, the method of generating arrays described in U.S. Pat. No. 6,127,129 (herein incorporated by reference) is utilized. In the first step of the method, a monolayer of a thiol is self-assembled from an ethanolic solution onto a solid support, which has been coated with a thin noble-metal film. The present invention is not limited to a particular thiol. A variety of lengths and positions of attachment of the thiol group are contemplated as being suitable for use in the present invention. In some preferred embodiments, long chain (e.g., 11 carbon) alkanethiols are utilized. In other embodiments, branched or cyclic thiols are utilized.

In some embodiments, amine (e.g., MUAM) or carboxylic acid terminated (e.g., MUA), hydroxyl terminated (e.g., MUD), or MUAM modified to be thiol terminated are utilized. In some particularly preferred embodiments, an ω-modified alkanethiol, preferably an amine-terminated alkanethiol, most preferably 11-mercaptoundecylamine (MUAM), is utilized (See e.g., Thomas et al., J Am. Chem. Soc. 117:3830 [1995]).

Self-assembled monolayers of ω-modified alkanethiols on gold form well ordered, monomolecular films. However, if left exposed for extended periods of time, the terminal amine groups of amino-modified alkanthiols may react with $CO_2$ to form carbamate salts on the surface. Consequently, it is preferred that exposure of amino-terminated alkanethiol-coated substrates to $CO_2$ be minimized.

Next, the alkanethiol-covered surface is reacted with a reversible protecting group to create a hydrophobic surface. In certain embodiments utilizing an amine-modified alkanethiol such as MUAM, the protecting group is an amino protecting group, preferably 9-fluorenylmethoxycarbonyl (Fmoc). The present invention is not limited to an Fmoc protecting group. Any reversible protecting group may be utilized. Preferred protecting groups offer efficient protection, favorable (e.g., to biological molecules) deprotecting conditions, efficient deprotection, and are suitable for reactions on a surface. For example, in some embodiments, Tboc is utilized for the protection of alkanethiols.

Fmoc is a bulky, hydrophobic, base labile, amine protecting group routinely used in the solid phase synthesis of peptides. The choice of protecting group used is dependent in large measure upon the nature of the ω-modification made to the alkanethiol. If the ω-modification is the addition of a carboxyl group, a hydrophobic carboxy protecting group is preferred. Likewise, if the ω-modification is the addition of a hydroxyl or thiol group, a hydrophobic hydroxy or thiol protecting group, respectively, is preferred used. Any type of hydrophobic protecting group suitable for protecting the ω-modification used on the alkanethiol can be utilized in the present invention. Numerous such protecting groups, for any number of reactive moieties, such as amine, hydroxy, ester, carbamate, amides, ethers, thioethers, thioesters, acetals, ketals and carboxy functionalities, are known to the art (See e.g., Frutos et al., Langmuir 16:2192 [2000]). For example, chloride derivatives of both Fmoc and trityl can be used to reversibly modify hydroxyl-terminated alkanethiols.

In some embodiments utilizing Fmoc protecting groups, the N-hydroxysuccinimide ester of Fmoc (Fmoc-NHS) is reacted with the terminal amine moiety of the MUAM molecule to form a stable carbamate (urethane) linkage, covalently attaching the Fmoc group to the surface.

Subsequently, the bond anchoring the alkanethiol to the metal substrate is selectively cleaved to yield a patterned surface of exposed metal. In some preferred embodiments, UV photopatterning is utilized to create the patterned surface. However, any suitable method of generating a patterned surface may be utilized. For example, in some embodiments, microcontact printing methods can also be used to yield a patterned surface. Using UV patterning, the surface is exposed through a quartz mask to UV radiation, which photo-oxidizes the gold-sulfur bond that anchors the alkanethiol monolayers to the surface. The surface is then rinsed, removing the photo-oxidized alkanethiol and leaving an array of bare metal pads surrounded by a hydrophobic MUAM+Fmoc background. Using photopatterning, features with dimensions as small as 50 μm have been achieved; using microcontact printing methods, arrays with features as small as about 100 nm are achievable.

The surface is next exposed to an alkanethiol solution (in some preferred embodiments, an ethanolic solution of MUAM) whereby the alkanethiol assembles into the bare gold regions producing a surface composed of hydrophilic alkanethiol pads surrounded by the hydrophobic blocked background. This difference in hydrophobicity between the reactive alkanethiol regions and the background is useful for the pinning of small volumes of aqueous biomolecule or cell solutions onto individual array locations.

Biological macromolecules are then covalently arrayed on the surface. The alkanethiol active pads are first exposed to a solution of a bifunctional linker. Preferred linkers are those capable of binding at one end to the alkanethiol surface and at the other end to the biological macromolecule to be immobilized to form the desired array. Any bifunctional (e.g., hetero or homo bifunctional) linker having these characteristics can be used in the present invention (See e.g., Smith et al., Langmuir 17:2502 [2001] and the Catalog of Pierce Chemical Company, Rockford, Ill.). Exemplary linkers include, but are not limited to, SSMCC, DSS, and PDITC.

The preferred bifunctional linker is sulfosuccinimidyl 4-(N-maleimidomethyl)cyclohexane-1-carboxylate (SSMCC), a heterobifunctional linker which contains both an N-hydroxysulfosuccinimide (NHSS) ester and a maleimide functionality. The NHSS ester end of the molecule reacts with the free amine groups on an amino-modified surface, such as the MUAM spots, creating pads terminated in maleimide groups, which are reactive towards thiols. Small volumes (0.08 to 0.1 L) of 1 mM solutions of 5'-thiol-modified biological macromolecules (e.g., DNA sequences) are then spotted at discrete array locations and react to form a covalent attachment to the surface. Using this technique, any number of biological macromolecules can be spotted at different array locations.

The protecting group (e.g., Fmoc) is next removed from the array surface. Preferably, this is accomplished by exposure to a 1M solution of the secondary amine, TAEA, in DMF. Many basic secondary amines can be used to remove Fmoc from the surface (e.g., including, but not limited to, 1M solutions of ethanolamine and piperidine). After the deprotection step, the array background has been converted back to the original alkanethiol surface.

In the final step of the array fabrication, the alkanethiol background is reacted with a compound to create a background that is resistant to the non-specific binding of proteins. The preferred compound for this purpose is PEG-NHS, although any compound that will selectively bind to the alkanethiol surface and inhibit non-selective protein binding can be used. In order to effectively monitor the binding of proteins to arrays of surface-bound biomolecules or cells, it is preferred that the array background prohibit the non-specific adsorption of protein molecules. Additional blocking groups include, but are not limited to, mixtures of PEG-terminated and other molecules (e.g., hydroxyl-terminated), different molecular weights of PEG molecules, polylysine, casein, BSA, and octadecane thiol (See e.g., Chapman et al., J. Am. Chem. Soc., 122:8303 [2000]).

2. Additional Arrays

The present invention is not limited to the array fabrication methods described above. Additional array generating technologies may be utilized, including, but not limited to, those described below.

For example, in some embodiments, arrays are be synthesized on glass or silicon surfaces. For creation of arrays on silicon surfaces, the methods described in U.S. application Ser. No. 09/659,442, incorporated herein by reference, may be used.

In some embodiments, a DNA array is generated using photolithography on a solid surface (Affymetrix, Santa Clara, Calif.; See e.g., U.S. Pat. Nos. 6,045,996; 5,925,525; and 5,858,659; each of which is herein incorporated by reference). The technology uses miniaturized, high-density arrays of oligonucleotide probes affixed to the solid surface. Probe arrays are manufactured by Affymetrix's light-directed chemical synthesis process, which combines solid-phase chemical synthesis with photolithographic fabrication techniques employed in the semiconductor industry. Using a series of photolithographic masks to define exposure sites, followed by specific chemical synthesis steps, the process constructs high-density arrays of oligonucleotides, with each probe in a predefined position in the array.

In other embodiments, a DNA array containing electronically captured probes (labeled nucleic acid sequences) (Nanogen, San Diego, Calif.) is utilized (See e.g., U.S. Pat. Nos. 6,017,696; 6,068,818; and 6,051,380; each of which are herein incorporated by reference). In some embodiments, a modified method of Nanogen's technology, which enables the active movement and concentration of charged molecules to and from designated test sites on a semiconductor microchip is utilized. DNA capture probes are electronically placed at, or "addressed" to, specific sites on the solid support. Since DNA has a strong negative charge, it can be electronically moved to an area of positive charge.

First, a test site or a row of test sites on the solid support is electronically activated with a positive charge. Next, a solution containing the DNA probes is introduced onto the solid support. The negatively charged probes rapidly move to the positively charged sites, where they concentrate and are chemically bound to a site on the solid support. The solid support is then washed and another solution of distinct DNA probes is added until the array of specifically bound DNA probes is complete.

In still further embodiments, an array technology based upon the segregation of fluids on a flat surface (chip) by differences in surface tension (ProtoGene, Palo Alto, Calif.) is utilized (See e.g., U.S. Pat. Nos. 6,001,311; 5,985,551; and 5,474,796; each of which is herein incorporated by reference). Protogene's technology is based on the fact that fluids can be segregated on a flat surface by differences in surface tension that have been imparted by chemical coatings. Once so segregated, oligonucleotide probes are synthesized directly on the surface by ink-jet printing of reagents. The array with its reaction sites defined by surface tension is mounted on a X/Y translation stage under a set of four piezoelectric nozzles, one for each of the four standard DNA bases. The translation stage moves along each of the rows of the array and the appropriate reagent is delivered to each of the reaction site. For example, the A amidite is delivered only to the sites where amidite A is to be coupled during that synthesis step and so on. Common reagents and washes are delivered by flooding the entire surface and removing by spinning. DNA probes unique for the target sequence of interest are affixed to the solid support using Protogene's technology. The prism is then contacted with a test sample of interest. Following hybridization, unbound DNA is removed and hybridization is detected using SPR.

3. Microfluidics

In some embodiments, arrays are fabricated by patterning the solid support with microfluidic channels. In some embodiments, microfluidics are generated using the polydimethylsiloxane (PDMS) polymer-based methods described by Lee et al. (Analytical Chemistry, 73:5525 [2001]). This technique can be used for both fabricating 1-D DNA microarrays using parallel microfluidic channels on chemically modified gold and silicon surfaces, and in a microliter detection volume methodology that uses 2-D DNA microarrays formed by employing the 1-D DNA microarrays in conjunction with a second set of parallel microfluidic channels for solution delivery.

For example, in some embodiments, microliter detection volume methodology that uses 2-D DNA hybridization microarrays formed by employing 1-D DNA line arrays in conjunction with a second set of parallel microfluidic channels for solution delivery is utilized. In some embodiments, PDMS microchannels are fabricated by replication from 3-D silicon wafer masters that were created photolithographically from 2-D chrome mask patterns (See e.g., Duffy et al., Anal. Chem., 70:4974 [1998] and Effenhauser et al., Anal. Chem., 69:3451 [1997]).

A gold thin film surface deposited on the solid support is reacted with MUAM in order to form a self-assembled monolayer on the gold surface as described above. A PDMS polymer film containing parallel microchannels is then arrayed on the MUAM modified gold surface. In some embodiments, a surface pattern is created by flowing the heterobifunctional linker SSMCC through the PDMS microchannels over the gold surface. The SSMCC reacts with the MUAM to create a maleimide-terminated alkanethiol monolayer. Biological macromolecules (e.g., 5'-thiol-modified DNA or RNA probes) are then each flowed into a separate PDMS microchannel and react with the maleimide-terminated gold surface to form an array of probes on the surface of the gold. In some embodiments, the microchannels are cleaned with water, the PDMS is removed from the surface and the gold slide is soaked in a PEG-NHS solution in order to modify the MUAM background (see above description of blocking with PEG-NHS). The PEG-coated background helps to eliminate nonspecific adsorption of DNA or RNA during hybridization experiments.

The present invention is not limited to a particular method of fabricating channels in the solid surfaces of the present invention. For example, in other embodiments, the present invention utilizes microchannels etched into the prism (See e.g., U.S. Pat. No. 6,176,962, herein incorporated by reference). In still further embodiments, microfluidic channels are fabricated using wet chemical etching (Wang et al., Anal. Chem., 72:2514 [2000]) or soft lithography (Deng et al., Anal. Chem. 72:3176 [2000]).

4. Array Processing

In some embodiments, following patterning or generation of arrays, a silicone gasket (Grace Biolabs, Bend, Oreg.) is sandwiched in-between the solid surface and a microscope cover slide to form a small reaction chamber. In other embodiments, a HYBRIWELL seal (Grace Biolabs) is used to create a low-volume reaction chamber.

II. In vitro Interaction Assays

In some embodiments, the present invention provides methods for performing in vitro molecular interaction assays. In some embodiments, one or more reaction components are arrayed on a solid support. In a classic "2-hybrid" assay (See e.g., U.S. Pat. Nos. 5,283,173 and 6,251,676, each of which is herein incorporated by reference), a first fusion protein that comprises a first candidate binding partner fused to a DNA binding domain, a second fusion protein comprising a second candidate binding partner fused to a transcription activation domain, and DNA target comprising a transcription activation sequence recognized by the DNA binding domain are utilized. The interaction of the binding partners results in the association of the DNA binding and transcription activation domains into a complex that can bind to the target DNA sequence and promote transcription (e.g., of a reporter gene) within a living cell. The methods of the present invention provide methods of performing such reaction in vitro, either in solution or on a solid support.

A. Two-Hybrid Reactions

In a typical yeast two hybrid system, three components interact to produce a signal. The components are a target DNA molecule containing a transcription factor binding site, a first fusion protein, and a second fusion protein. The first fusion protein contains a DNA binding domain and a first binding partner domain. The second fusion protein contains a second binding partner domain and an RNA polymerase activation domain. If the first and second binding partner domains interact with each other, a functional transcriptional activator is formed. Reconstitution of an active transcriptional activator allows transcription of the target DNA molecule. Transcription requires the cell's transcription machinery or the addition of required components to an in vitro reaction. Transcription of the target DNA molecule generates a signal, such as colony growth or a colony color change.

In some embodiments, of the present invention, the two hybrid system components are removed from the confines of a cell, and the interaction occurs in vitro. The first and second fusion proteins, and target DNA molecules are mixed under conditions where the components can interact. The components of an in vitro transcription system are further mixed with the two hybrid system components. The use of nuclear extracts to provide cell-free transcription systems are well known in the art (See e.g., the Promega 2002 Life Sciences Catalog, and Promega Techinal Bulletin 123 describing HeLa nuclear extracts for in vitro transcription, incorporated herein by reference). Instructions for making and using a yeast in vitro transcription system are available, for example, on the World Wide Web at the Internet Web site of the Hahn lab at the Fred Hutchinson Cancer Research center) As in the in vivo two hybrid system, if the first and second binding partners of the respective fusion proteins are capable of interaction, an RNA molecule is produced.

Fusion proteins that comprise a first candidate binding partner fused to a DNA binding domain will bind to their cognate target DNA sequences, either in solution or on a DNA array. In some preferred embodiments, an array of distinct target DNA molecules are arrayed on a solid support. In some preferred embodiments, several DNA binding domains that recognize and bind to specific DNA sequences are employed. A mixture of such fusion proteins can then be exposed to the target DNA, and the fusion proteins will automatically sort themselves to the appropriate address, as defined by the cognate DNA molecules, on the array. In other embodiments, one or a small number of DNA binding domains are utilized. In these embodiments, creation of an addressed array of fusion proteins is obtained by spotting the fusion proteins at known locations on the array. In some embodiments, the second binding partner fusion protein is added to the first binding partner fusion protein prior to exposing the array to the first fusion protein binding partner, the first and second fusion proteins are allowed to interact, and the mixture is exposed to the array. In other preferred embodiments, the second binding partner fusion protein is exposed to the array following exposure of the array to the first binding partner fusion protein. In other embodiments, the first or second fusion protein is arrayed on the solid support (e.g., via a linker).

The present invention is not limited to particular binding partners, unlike cellular systems where the binding partners must be proteins. Any two molecules suspected or known to interact may be utilized. In some embodiments, both of the binding partners are proteins. For example in some embodiments, binding partners include, but are not limited to, transcription factors (e.g., hetero or homo multimeric transcription factors), receptor/ligand pairs (e.g., including, but not limited to, hormone receptors/hormones, G-protein receptors/G-proteins, intracellular trafficking signaling molecules, and drug receptors), cellular signaling molecules (e.g., including, but not limited to, kinases, phosphatases, oncogene products), and antibody/antigen interactions.

In other embodiments, binding partners are nucleic acids (e.g., RNA or DNA) and or carbohydrates. In yet other embodiments, one of the binding partners is a protein and the other is a small molecule (e.g., including but not limited to potential drugs, phosphates, sulfates, carboxylates, lipids, cartilage, or basement membrane components). In yet other embodiments, both of the binding partners are small molecules.

The present invention is also not limited to the use of transcription activation domains fused to binding partners. Any protein interaction assay that results in a detectable signal and can be performed on a solid support may be utilized. For example, in some embodiments, fluorescence complementation interaction assays are utilized (See e.g., WO 01/87919 and Hu et al., Molec. Cell., 9:789 [2002], herein incorporated by reference).

B. Detection of Interaction

1. Direct Detection

In some embodiments, the interaction between the first and second candidate binding partner fusion proteins is measured without further signal amplification. In one embodiment, binding of the second candidate binding partner to the first candidate binding partner is detected by SPR. In another embodiment, either the first or second candidate binding partner is fluorescently labeled. Binding of the labeled candidate binding partner is then measured using a fluorescent imaging device.

2. Signal Amplification

In some embodiments, a means to amplify the signal produced by the interaction is provided. In some embodiments, components of an in vitro transcription assay are further provided with the first and second fusion proteins and cognate target DNA molecule. Interaction between the first and second fusion protein reconstitutes a functional transcriptional activator, which then allows transcription from the cognate DNA template to occur. In some embodiments, the transcription reaction occurs in solution. In some embodiments, the transcription reaction is conducted on the solid support. In some embodiments, the DNA is arrayed on the solid surface. In other embodiments, the transcription reactions are performed in a separate vessel in solution or in a cell. Detection of the RNA synthesized from the target template can then be performed on a solid surface. Alternatively, the RNA synthesis reaction may incorporate fluorescent or radioactive tags, and the reaction may be monitored for production of a labeled polynucleotide. In some embodiments, following the two-hybrid reaction, RNA expression is detected using any suitable method including, but not limited to SPR, fluorescence, FRET, electrophoretic methods, and RT-PCR.

For example, in some embodiments, RNA expression is detected on the same solid support as the reaction. In some embodiments, RNA is detected at the site of transcription. In some embodiments, for detection at the site of RNA transcription, a mixture of double-stranded DNA template and single-stranded detection molecules is attached at each feature of the array. In some embodiments, using SPR, the nascent RNA is detected by its hybridization to the single-stranded complement. Because of the stronger hybridization of RNA-DNA duplexes relative to DNA-DNA duplexes, in some embodiments, hybridization of the nascent RNA to a self-complementary DNA FRET probe is used to detect the RNA molecule. The RNA will out-compete the self complementary DNA for hybridization. In some embodiments, the FRET quenching dye is designed within the hybridization region, and the detected fluor is linked near the end of the DNA molecule. Hybridization of the RNA thus leads to the separation of quencher and fluor dyes, which is detected by an increase in fluorescence. In other embodiments, RNA expression is detected on a separate feature of the array (e.g., by flowing reaction products from one site on the array to another using microfluidics). In some embodiments, RT-PCR amplification of the nascent RNA molecule is employed to further amplify weak signals.

In other embodiments, signal enhancement utilizes label-free detection methods (e.g., the label free electrical detection method described in WO 01/61053A2 (herein incorporated by reference). In still further embodiments, oligonucleotide-conjugated nanoparticles are utilized for detection of binding (See e.g., Nanosphere, Northbrook, Ill., U.S. Pat. No. 6,361,944, herein incorporated by reference). The assay involves a detectable change (e.g., a color change, the formation of aggregates of the nanoparticles, or the precipitation of the aggregated nanoparticles) that occurs upon hybridization of the oligonucleotides on the nanoparticles to the nucleic acid may be. The color changes can be observed with the naked eye or spectroscopically. The formation of aggregates of the nanoparticles can be observed by electron microscopy or by nephelometry. The precipitation of the aggregated nanoparticles can be observed with the naked eye or microscopically.

In other embodiments, RNA is detected off of the solid support by any suitable method, including, but not limited to, by hybridization to a labeled probe (e.g., a Northern blot) and reverse-transcriptase PCR (RT-PCR).

In still further embodiments, where transcription reactions are conducted off of the solid support, RNA is detected using chip-based methods. Direct detection of the reporter RNA decreases the time to results of a typical two-hybrid experiment by six days. Chip-based detection further provides the benefit of eliminating costly culture media and supplies.

III. Applications

The methods of the present invention find use in the detection of a variety of molecular interactions. The methods of the present invention find use in the analysis of any molecular interaction between two or more molecules.

A. Screening for Novel Binding Partners

In some embodiments, the methods of the present invention are used to screen for novel binding proteins that interact with a known first binding partner. For example, in some embodiments, genetic libraries (e.g., from a particular organism or cell type) are cloned into expression vectors that express a fusion protein of the unknown protein and a DNA binding or polymerase activation domain. The interaction of the library of fusion protein is then screened for interaction with the known binding partner using any suitable method (e.g., including, but not limited to, the methods disclosed herein).

Fusion proteins identified by the methods of the present invention as interacting with the known binding partner may be further analyzed using standard molecular biology methods. For example, in some embodiments, addressable arrays are utilized so that a particular spot or region that gives a positive interaction signal can be identified. Fusion proteins at that spot can then be isolated and characterized (e.g., protein binding partners can be identified by peptide sequencing followed by the generation of primers for isolation of the nucleic acid sequence encoding the protein). In other embodiments, the identity of the binding partner at each location of the array is predetermined, allowing for easy identification of the binding partner.

B. Drug Screening

In other embodiments, binding partners known to interact are utilized in the screening of compounds that alter (e.g., inhibit or enhance) the interaction. In some embodiments, the test compound is a drug or drug lead compound. The level of transcription in the presence of the compound is compared to the level in its absence.

In other embodiments, binding partners that are known to interact poorly are chosen for assay. Compounds are then screened for their ability to enhance the interaction.

C. Combinatorial Assays

In still further embodiments, the assays of the present invention are utilized in high throughput or combinatorial assays. For example, to query multiple first binding partners against multiple second binding partners, the first fusion partner is immobilized, and the surface array is monitored for interaction of the first and second fusion proteins (e.g., with SPR or fluorescence). Upon binding, RNA is transcribed, indicating which first fusion protein was responsible for the binding. In some embodiments, such an assay is performed in a linear array using microfluidics. In some embodiments, different DNA binding domains are employed, so that different template DNAs, and thus detectably different output RNAs, are produced.

We claim:

1. A composition comprising a solid surface, said solid surface comprising arrayed nucleic acids, at least one first protein bound to at least one of said arrayed nucleic acids, and a second protein bound to said first protein; wherein said first protein is a first fusion protein, said first fusion protein comprising a DNA binding domain fused to a first binding partner, wherein said DNA binding domain is capable of binding to said target nucleic acid sequence; wherein said second protein is a second fusion protein, said second fusion protein comprising an RNA polymerase activation domain fused to a second binding partner, wherein said second binding partner is capable of interacting with said first binding partner.

2. The composition of claim 1, wherein said arrayed nucleic acids comprise an array of target nucleic acid sequences.

3. The composition of claim 1, wherein said solid support is a metal, glass or silicon surface.

4. The composition of claim 3, wherein said metal surface is deposited on an SPR prism.

5. The composition of claim 1, wherein said array of target nucleic acid sequences comprises at least 20 different nucleic acid sequences.

6. The composition of claim 1, wherein said array of target nucleic acid sequences comprises at least 50 different nucleic acid sequences.

7. The composition of claim 1, wherein said array of target nucleic acid sequences comprises at least 100 different nucleic acid sequences.

8. The composition of claim 1, wherein said array of target nucleic acid sequences comprises at least 1000 different nucleic acid sequences.

9. The composition of claim 1, further comprising a plurality of first fusion proteins, wherein each of said plurality of fusion proteins comprises a different first binding partner.

10. The composition of claim 1, further comprising a plurality of second fusion proteins, wherein each of said plurality of fusion proteins comprises a different second binding partner.

11. The composition of claim 1, wherein said solid support further comprises a plurality of microfluidic channels.

12. The composition of claim 1, wherein said sold support further comprises a plurality of etched microchannels.

13. The composition of claim 1, wherein said first binding partner is selected from the group consisting of a peptide, a polypeptide, a nucleic acid, a carbohydrate, a lipid, and a small molecule.

14. The composition of claim 1, wherein said second binding partner is selected from the group consisting of a peptide, a polypeptide, a nucleic acid, a carbohydrate, a lipid, and a small molecule.

15. The composition of claim 1, further comprising an antibody bound to said second protein.

16. A composition comprising a solid surface comprising a plurality of microfluidic channels, said solid surface comprising arrayed nucleic acids, at least one first protein bound to at least one of said arrayed nucleic acids, and a second protein bound to said first protein; wherein said first protein is a first fusion protein, said first fusion protein comprising a DNA binding domain fused to a first binding partner, wherein said DNA binding domain is capable of binding to said target nucleic acid sequence; wherein said second protein is a second fusion protein, said second fusion protein comprising an RNA polymerase activation domain fused to a second binding partner, wherein said second binding partner is capable of interacting with said first binding partner.

17. A composition comprising a solid surface comprising a plurality of etched microchannels, said solid surface comprising arrayed nucleic acids, at least one first protein bound to at least one of said arrayed nucleic acids, and a second protein bound to said first protein; wherein said first protein is a first fusion protein, said first fusion protein comprising a DNA binding domain fused to a first binding partner wherein said DNA binding domain is capable of binding to said target nucleic acid sequence; wherein said second protein is a second fusion protein, said second fusion protein comprising an RNA polymerase activation domain fused to a second binding partner, wherein said second binding partner is capable of interacting with said first binding partner.

18. A composition comprising a solid surface, said solid surface comprising arrayed nucleic acids, at least one first protein bound to at least one of said arrayed nucleic acids, a second protein bound to said first protein, and an antibody bound to said second protein; wherein said first protein is a first fusion protein, said first fusion protein comprising a DNA binding domain fused to a first binding partner, wherein said DNA binding domain is capable of binding to said target nucleic acid sequence; wherein said second protein is a second fusion protein, said second fusion protein comprising an RNA polymerase activation domain fused to a second binding partner, wherein said second binding partner is capable of interacting with said first binding partner.

19. A composition comprising a solution of target nucleic acids, at least one first fusion protein bound to at least one of said nucleic acids, and a second fusion protein bound to at least one of said first proteins; wherein said first fusion protein comprises a DNA binding domain fused to a first binding partner, wherein said DNA binding domain is capable of binding to said target nucleic acid sequence; wherein said second fusion protein comprises an RNA polymerase activation domain fused to a second binding partner, wherein said second binding partner is capable of interacting with said first binding partner.

20. The composition claim 19, further comprising an RNA transcribed from at least one of said target nucleic acids.

21. A system for the detection of molecular interactions, comprising
 a) a solid support comprising an array of target nucleic acid sequences; and
 b) a first fusion protein comprising a DNA binding domain fused to a first binding partner, wherein said DNA binding domain is capable of binding to said target nucleic acid sequence; and
 c) a second fusion protein comprising an RNA polymerase activation domain fused to a second binding partner, wherein said second binding partner is capable of interacting with said first binding partner.

22. The system of claim 21, wherein said solid support is a metal surface.

23. The system of claim 22, wherein said metal surface is deposited on an SPR prism.

24. The system of claim 21, wherein said array of target nucleic acid sequences comprises at least 20 different nucleic acid sequences.

25. The system of claim 21, wherein said array of target nucleic acid sequences comprises at least 50 different nucleic acid sequences.

26. The system of claim 21, wherein said array of target nucleic acid sequences comprises at least 100 different nucleic acid sequences.

27. The system of claim 21, wherein said array of target nucleic acid sequences comprises at least 1000 different nucleic acid sequences.

28. The system of claim 21, further comprising a plurality of first fusion proteins, wherein each of said plurality of fusion proteins comprises a different first binding partner.

29. The system of claim 21, further comprising a plurality of second fusion proteins, wherein each of said plurality of fusion proteins comprises a different second binding partner.

30. The system of claim 21, further comprising an antibody capable of specifically binding to said second fusion protein.

31. The system of claim 21, wherein said solid support further comprises a plurality of microfluidics channels.

32. The system of claim 21, wherein said solid support further comprises a plurality of etched microchannels.

33. The system of claim 21, wherein said first binding partner is selected from the group consisting of a peptide, a polypeptide, a nucleic acid, a carbohydrate, a lipid and a small molecule.

34. The system of claim 21, wherein said second binding partner is selected from the group consisting of a peptide, a polypeptide, a nucleic acid, a carbohydrate, a lipid, and a small molecule.

35. The system of claim 21, further comprising at least one test compound.

36. The system of claim 35, wherein said test compound is a drug.

37. The system of claim 21, further comprising an apparatus capable of detecting an interaction between said first fusion protein, and said second fusion protein.

38. A system for the detection of molecular interactions, comprising
　a) a solid support comprising an array of a first fusion proteins, wherein each of said first fusion proteins comprises a DNA binding domain fused to a first binding partner;
　b) a second fusion protein comprising an RNA polymerase activation domain fused to a second binding partner, wherein said second binding partner is capable of interacting with said first binding partner; and
　c) at least one target nucleic acid sequence wherein said target sequence is capable of being bound by said DNA binding domain.

39. A system for the detection of molecular interactions, comprising
　a) a solid support comprising an array of microfluidic channels, said sold support further comprising an array of target nucleic acid sequences; and
　b) a first fusion protein comprising a DNA binding domain fused to a first binding partner, wherein said DNA binding domain is capable of binding to said target nucleic acid sequence; and
　c) a second fusion protein comprising an RNA polymerase activation domain fused to a second binding partner, wherein said second binding partner is capable of interacting with said first binding partner.

40. A system for the detection of molecular interactions, comprising
　a) a solid support comprising an array of etched microchannels, said solid support further comprising an array of target nucleic acid sequences; and
　b) a first fusion protein comprising a DNA binding domain fused to a first binding partner, wherein said DNA binding domain is capable of binding to said target nucleic acid sequence; and
　c) a second fusion protein comprising an RNA polymerase activation domain fused to a second binding partner, wherein said second binding partner is capable of interacting with said first binding partner.

41. A system for the detection of molecular interactions, comprising:
　a) a solution of at least one target nucleic acid sequence; and
　b) a first fusion protein comprising a DNA binding domain fused to a first binding partner, wherein said DNA binding domain is capable of binding to said target nucleic acid sequence; and
　c) a second fusion protein comprising an RNA polymerase activation domain fused to a second binding partner, wherein said second binding partner is capable of interacting with said first binding partner.

42. A method of detecting interactions between biological molecules, comprising:
　a) providing
　　i) a solid support comprising an array of target nucleic acid sequences; and
　　ii) a first protein capable of interacting with said target nucleic acid sequence; wherein said first protein comprises a first fusion protein comprising a DNA binding domain fused to a first binding partner, wherein said DNA binding domain is capable of binding to said target nucleic acid sequence;
　　iii) a second protein capable of interacting with said protein; wherein said second protein comprises a second fusion protein comprising an RNA polymerase activation domain fused to a second binding partner, wherein said second binding partner is capable of interacting with said first binding partner, and
　　iv) a system configured for the detection of RNA transcribed from said target nucleic acid sequences; and
　b) contacting said first and second fusion proteins with said solid support under conditions such that said first and second proteins are capable of interacting;
　c) detecting the presence or absence of RNA transcribed from said target nucleic acid sequence with said system, wherein said presence of said RNA is the result of an interaction between said first and second proteins.

43. The method of claim 42, wherein said detection system is selected from the group consisting of a fluorescence detection system, a SPR detection system, a RT-PCR detection system, an electrophoresis detection system, and a hybridization detection system.

44. The method of claim 42, wherein said solid support is a metal surface.

45. The method of claim 44, wherein said metal surface is deposited on an SPR prism.

46. The method of claim 42, wherein said array of target nucleic acid sequences comprises at least 20 different nucleic acid sequences.

47. The method of claim 42, wherein said array of target nucleic acid sequences comprises at least 50 different nucleic acid sequences.

48. The method of claim 42, wherein said array of target nucleic acid sequences comprises at least 100 different nucleic acid sequences.

49. The method of claim 42, wherein said array of target nucleic acid sequences comprises at least 1000 different nucleic acid sequences.

50. The method of claim 42, further comprising a plurality of first fusion proteins, wherein each of said plurality of fusion proteins comprises a different first binding partner.

51. The method of claim 42, further comprising a plurality of second fusion proteins, wherein each of said plurality of fusion proteins comprises a different second binding partner.

52. The method of claim 42, wherein said solid support further comprises a plurality of microfluidics channels.

53. The method of claim 42, wherein said first binding partner is selected from the group consisting of a peptide, a polypeptide, a nucleic acid, a carbohydrate, a lipid and a small molecule.

54. The method of claim 42, wherein said second binding partner is selected from the group consisting of a peptide, a polypeptide, a nucleic acid, a carbohydrate, a lipid and a small molecule.

55. A method of detecting interactions between biological molecules, comprising:
   a) providing
      i) a solid support comprising a plurality of microfluidic channels, said solid support further comprising an array of target nucleic acid sequences; and
      ii) a first protein capable of interacting with said target nucleic acid sequence; wherein said first protein comprises a first fusion protein comprising a DNA binding domain fused to a first binding partner, wherein said DNA binding domain is capable of binding to said target nucleic acid sequence;
      iii) a second protein capable of interacting with said protein; wherein said second protein comprises a second fusion protein comprising an RNA polymerase activation domain fused to a second binding partner, wherein said second binding partner is capable of interacting with said first binding partner; and
      iv) a system configured for the detection of RNA transcribed from said target nucleic acid sequences; and
   b) contacting said first and second fusion proteins with said solid support under conditions such that said first and second proteins are capable of interacting;
   c) detecting the presence or absence of RNA transcribed from said target nucleic acid sequence with said system, wherein said presence of said RNA is the result of an interaction between said first and second proteins.

56. A method of detecting interactions between biological molecules, comprising:
   a) providing
      i) a solid support comprising a plurality of etched microchannels, said solid support further comprising an array of target nucleic acid sequences; and
      ii) a first protein capable of interacting with said target nucleic acid sequence; wherein said first protein comprises a first fusion protein comprising a DNA binding domain fused to a first binding partner, wherein said DNA binding domain is capable of binding to said target nucleic acid sequence;
      iii) a second protein capable of interacting with said protein; wherein said second protein comprises a second fusion protein comprising an RNA polymerase activation domain fused to a second binding partner, wherein said second binding partner is capable of interacting with said first binding partner; and
      iv) a system configured for the detection of RNA transcribed from said target nucleic acid sequences; and
   b) contacting said first and second fusion proteins with said solid support under conditions such that said first and second proteins are capable of interacting;
   c) detecting the presence or absence of RNA transcribed from said target nucleic acid sequence with said system, wherein said presence of said RNA is the result of an interaction between said first and second proteins.

57. A method of detecting interactions between biological molecules, comprising:
   a) providing
      i) a solid support comprising an array of target nucleic acid sequences; and
      ii) a first protein capable of interacting with said target nucleic acid sequence; wherein said first protein comprises a first fusion protein comprising a DNA binding domain fused to a first binding partner, wherein said DNA binding domain is capable of binding to said target nucleic acid sequence;
      iii) a second protein capable of interacting with said protein; wherein said second protein comprises a second fusion protein comprising an RNA polymerase activation domain fused to a second binding partner, wherein said second binding partner is capable of interacting with said first binding partner; and
      iv) a system configured for the label-free detection of RNA transcribed from said target nucleic acid sequences; and
   b) contacting said first and second fusion proteins with said solid support under conditions such that said first and second proteins are capable of interacting;
   c) detecting the presence or absence of RNA transcribed from said target nucleic acid sequence with said system, wherein said presence of said RNA is the result of an interaction between said first and second proteins.

58. A method of detecting molecular interactions, composing:
   a) providing
      i) a solid surface comprising an array of target nucleic acids;
      ii) at least one first protein; capable of interacting with said target nucleic acids; wherein said first protein comprises a first fusion protein comprising a DNA binding domain fused to a first binding partner, wherein said DNA binding domain is capable of binding to said target nucleic acids;
      iii) at least one second protein capable of interacting with said first protein; wherein said second protein comprises a second fusion protein comprising an RNA polymerase activation domain fused to a second binding partner, wherein said second binding partner is capable of interacting with said first binding partner, said second protein further comprising an epitope for an antibody;
      iv) at least one antibody; and
      v) a system configured for detecting an interaction of said second protein and said antibody; and
   b) contacting said first protein and said second protein under conditions such that said first and second proteins are capable of interacting;
   c) contacting said interacting first and second proteins with said arrayed nucleic acids;
   d) contacting said at least one antibody with said second protein; and
   e) detecting the interaction of said first protein and said second protein using said apparatus.

59. A method of detecting interactions between biological molecules, comprising:
a) providing
  i) at least one target nucleic acid sequence in solution; and
  ii) a first protein capable of interacting with said target nucleic acid sequence; wherein said first protein comprises a first fusion protein comprising a DNA binding domain fused to a first binding partner, wherein said DNA binding domain is capable of binding to said target nucleic acid sequence;
  iii) a second protein capable of interacting with said first protein: wherein said second protein comprises a second fusion protein comprising an RNA polymerase activation domain fused to a second binding partner, wherein said second binding partner is capable of interacting with said first binding partner;
  iv) a system configured for the detection of RNA transcribed from said target nucleic acid sequences, wherein said system comprises a solid support configured for the detection of said RNA transcribed from said target nucleic acid sequence; and
b) contacting said first and second fusion proteins with said target nucleic acid solution under conditions such that said first and second proteins are capable of interacting;
c) detecting the presence or absence of RNA transcribed from said target nucleic acid sequence with said system, wherein said presence of said RNA is the result of an interaction between said first and second proteins.

60. A method of screening compounds, comprising:
a) providing
  i) a solid support comprising an array of target nucleic acid sequences; and
  ii) a first fusion protein comprising a first binding partner fused to a DNA binding domain, wherein said DNA binding domain is capable of binding to said target nucleic acid sequence;
  iii) a second fusion protein comprising an RNA polymerase activation domain fused to a second binding partner, wherein said second binding partner is capable of interacting with said first binding partner;
  iv) a system configured for the detection of RNA transcribed from said target nucleic acid sequences; and
  v) at least one test compound; and
b) contacting said test compound, and said first and second fusion proteins with said solid support under conditions such that said first and second binding partners are capable of interacting;
c) detecting the presence or absence of RNA transcribed from said target nucleic acid sequence using said system, wherein the presence of said RNA is the result of an interaction between said first and second binding partners.

61. The method of claim 60, further comprising the step of comparing the level of RNA transcribed from said target nucleic acid sequence in the presence of said test compound to the level of transcription in the absence of said test compound.

62. The method of claim 60, wherein said test compound is a drug.

63. The method of claim 60, wherein said detection system is selected from the group consisting of a fluorescence detection system, a SPR detection system, a RT-PCR detection system, an electrophoresis detection system, and a hybridization detection system.

64. The method of claim 60, wherein said solid support is a metal surface.

65. A method of screening compounds, comprising:
a) providing
  i) a solid support comprising a array of first proteins; wherein said first proteins comprise a first fusion protein comprising a DNA binding domain fused to a first binding partner;
  ii) at least one second protein, wherein said second protein is capable of interacting with said first protein; wherein said second protein comprises a second fusion protein comprising an RNA polymerase activation domain fused to a second binding partner, wherein said second binding partner is capable of interacting with said first binding partner;
  iii) at least one target nucleic acid sequence, wherein said target nucleic acid sequence is capable of interacting with said array of first proteins; and
  iv) a system configured for the detection of RNA transcribed from said target nucleic acid sequences; and
  v) at least one test compound; and
b) contacting said test compound, and said first and second fusion proteins with said solid support under conditions such that said first and second binding partners are capable of interacting;
c) detecting the presence or absence of RNA transcribed from said target nucleic acid sequence using said system, wherein the presence of said RNA is the result of an interaction between said first and second binding partners.

* * * * *

SEQUENCE LISTING

<160> NUMBER OF SEQ ID NOS: 4

<210> SEQ ID NO 1
<211> LENGTH: 29
<212> TYPE: DNA
<213> ORGANISM: Artificial Sequence
<220> FEATURE:
<223> OTHER INFORMATION: Synthetic

<400> SEQUENCE: 1
ggtagcgcat gcgtcagtcg tcgtctgga                              29

<210> SEQ ID NO 2
<211> LENGTH: 25
<212> TYPE: DNA
<213> ORGANISM: Artificial Sequence
<220> FEATURE:
<223> OTHER INFORMATION: Synthetic

<400> SEQUENCE: 2
ggtagcgcat gcgtcagtcg tcctc                                  25

<210> SEQ ID NO 3
<211> LENGTH: 9
<212> TYPE: RNA
<213> ORGANISM: Artificial Sequence
<220> FEATURE:
<223> OTHER INFORMATION: Synthetic

<400> SEQUENCE: 3 ccaucgcgu                                                    9

<210> SEQ ID NO 4
<211> LENGTH: 9
<212> TYPE: RNA
<213> ORGANISM: Artificial Sequence
<220> FEATURE:
<223> OTHER INFORMATION: Synthetic

<400> SEQUENCE: 4 ugcgcuacc                                                    9